(12) United States Patent
Li

(10) Patent No.: US 10,777,325 B1
(45) Date of Patent: Sep. 15, 2020

(54) SELF-GOVERNED INDIVIDUAL SOCIAL SAFE DETERMINATION AND CONFIRMATION METHOD AND SYSTEM

(71) Applicant: Zhaoyang Li, San Jose, CA (US)

(72) Inventor: Zhaoyang Li, San Jose, CA (US)

( * ) Notice: Subject to any disclaimer, the term of this patent is extended or adjusted under 35 U.S.C. 154(b) by 0 days.

(21) Appl. No.: 16/875,179

(22) Filed: May 15, 2020

Related U.S. Application Data

(60) Provisional application No. 63/017,136, filed on Apr. 29, 2020.

(51) Int. Cl.
*G16H 50/80* (2018.01)
*H04W 4/20* (2018.01)

(52) U.S. Cl.
CPC .............. *G16H 50/80* (2018.01); *H04W 4/20* (2013.01)

(58) Field of Classification Search
CPC ........ G16H 50/80; G16H 50/00; G16H 50/30; G16H 40/67; G16H 50/70; G16H 40/63; G16H 10/60; H04W 4/20
USPC ......... 455/414.1–414.2, 456.1–457; 705/2–3
See application file for complete search history.

(56) References Cited

U.S. PATENT DOCUMENTS

| | | | |
|---|---|---|---|
| 2012/0244886 A1* | 9/2012 | Blom | G16H 50/80 455/456.3 |
| 2015/0100330 A1* | 4/2015 | Shpits | G16H 50/80 705/2 |
| 2017/0039339 A1* | 2/2017 | Bitran | G16H 50/70 |
| 2018/0366230 A1* | 12/2018 | Pulitzer | G16H 50/70 |

\* cited by examiner

*Primary Examiner* — Michael Y Mapa

(57) ABSTRACT

The present invention provides a method, software program and a system for social safe determination and mutual identification such that individuals can meet and social with another with no or minimized risk exposure to COVID-19 virus or other infectious diseases through social or intimacy contact.

13 Claims, 4 Drawing Sheets

SELF-GOVERNED INDIVIDUAL SOCIAL SAFE DETERMINATION AND CONFIRMATION METHOD AND SYSTEM

CROSS-REFERENCE TO RELATED APPLICATION

This application claims the benefit of U.S. provisional application No. 63/017,136, filed Apr. 29, 2020, the teaching of which is incorporated herein by reference in its entirety.

FIELD OF THE INVENTION

The present invention relates to a method, system, and use for self-governed individual health state, e.g., social safe, determination, confirmation.

BACKGROUND OF THE INVENTION

Social life comes to halt in this COVID-19 pandemic. It is expected that COVID-19 will become cyclic epidemic as is flu. Since COVID-19 causes whole body damage to all organs to about 10-20% of the population who are infected with COVID-19, and vaccine, which is under development, is still years away. Additionally, even with vaccine in place, there is still a considerable size of the population that vaccination would not protect, as such, COVID-19 infection would be a social negative factor in the foreseeable future.

Efforts are being made to track COVID-19 infected individuals. An example is a tracking system implemented in South Korea, which uses information of infected individuals in a national data center to locate whereabouts of such infected individuals and digitally warn nearby people to keep a safe distance from the infected individual(s). Reportedly, Google and Apple are working together to generate a voluntary reporting system that functions similarly to what is implemented in South Korea, that is, to warn nearby people of COVID-19 infected individuals.

However, privacy is a major concern in both the South Korean and Apple/Google tracking systems as COVID-19 infection would perceivably carry with it a social stigma. As such, there is a reasonable doubt that the Google/Apple voluntary tracking system would fail.

Therefore, there is a need to have a method and system that can identify the state of COVID-19 infection of an individual such that we can adopt proper social distancing.

The embodiments below address the above-identified issues and needs.

SUMMARY OF THE INVENTION

In one aspect of the present invention, it is provided a method of social a method of social safe confirmation, comprising:

a) inputting a social safe signal data to a portable device by a user of the portable device, b) validating the social safe signal data using a validation control protocol to validate and output the social safe signal, the social safe signal being indicative of a negative state of infection of a disease, c) transmitting the social safe signal validated in b) to a nearby device upon request or pairing command and receiving information of a social safe signal of the nearby device, d) evaluating the social safe signal of the portable device and the social safe signal of the nearby device, and e) confirming as social safe and outputting as such if the social safe signal of the portable device and the social safe signal of the nearby device read the same and confirming as social non-safe and outputting as such if the social safe signal of the portable device and the social safe signal of the nearby device are different.

In some embodiments of the invention method, optionally in combination with any or all the various embodiments disclosed herein, inputting a social safe signal to a portable device is achieved by scanning a bar code, an image of document, or test strip or by manual inputting.

In some embodiments of the invention method, optionally in combination with any or all the various embodiments disclosed herein, the disease is COVID-19 infection or a sexually transmitted disease.

In some embodiments of the invention method, optionally in combination with any or all the various embodiments disclosed herein, the portable device is a smart phone or a note pad.

In some embodiments of the invention method, optionally in combination with any or all the various embodiments disclosed herein, the disease is HIV infection, HBv infection, or HBC infection.

In some embodiments of the invention method, optionally in combination with any or all the various embodiments disclosed herein, the social safe signal data is obtained by a COVID-19 virus RNA PCR test, by a blood IgG/IgM antibody test, by a saliva test, or by a stool test.

In some embodiments of the invention method, optionally in combination with any or all the various embodiments disclosed herein, the social safe signal data is obtained by a home testing kit.

In a second aspect of the present invention, it is provided a software program, comprising:

Module 100 configured to allow inputting a social safe signal data to a portable device by a user of the portable device, Module 200 configured to allow validating the social safe signal data using a validation control protocol to validate and output the social safe signal, the social safe signal being indicative of a negative state of infection of a disease, Module 300 configured to effect transmitting the social safe signal validated in b) to a nearby device upon request or pairing command and receiving information of a social safe signal of the nearby device, Module 400 configured to allow evaluating the social safe signal of the portable device and the social safe signal of the nearby device, and Module 500 configured to allow confirming as social safe and outputting as such if the social safe signal of the portable device and the social safe signal of the nearby device read the same and confirming as social non-safe and outputting as such if the social safe signal of the portable device and the social safe signal of the nearby device are different, wherein the software program is executable on the portable device.

In some embodiments of the invention software program, optionally in combination with any or all the various embodiments disclosed herein, Module 100 is configured to allow inputting a social safe signal to a portable device by scanning a bar code, an image of document, or test strip or by manual inputting.

In some embodiments of the invention software program, optionally in combination with any or all the various embodiments disclosed herein, the disease is COVID-19 infection or a sexually transmitted disease.

In some embodiments of the invention software program, optionally in combination with any or all the various embodiments disclosed herein, the portable device is a smart phone or a note pad.

In some embodiments of the invention software program, optionally in combination with any or all the various embodiments disclosed herein, the disease is HIV infection, HBv infection, or HBC infection.

In some embodiments of the invention software program, optionally in combination with any or all the various embodiments disclosed herein, the social safe signal data is obtained by a COVID-19 virus RNA PCR test, by a blood IgG/IgM antibody test, by a saliva test, or by a stool test.

In some embodiments of the invention software program, optionally in combination with any or all the various embodiments disclosed herein, the social safe signal data is obtained by a home testing kit.

In a further aspect of the present invention, it is provided a system, comprising a plurality of portable devices digitally linked to a server, wherein— the server is configured to receive and process social safe signal data that a user of a portable device elects to transmit to the server; and each of the portable devices comprises a software program executable on the portable device; and wherein the software program comprises:

Module 100 configured to allow inputting a social safe signal data to a portable device by a user of the portable device, Module 200 configured to allow validating the social safe signal data using a validation control protocol to validate and output the social safe signal, the social safe signal being indicative of a negative state of infection of a disease, Module 300 configured to effect transmitting the social safe signal validated in b) to a nearby device upon request or pairing command and receiving information of a social safe signal of the nearby device, Module 400 configured to allow evaluating the social safe signal of the portable device and the social safe signal of the nearby device, and Module 500 configured to allow confirming as social safe and outputting as such if the social safe signal of the portable device and the social safe signal of the nearby device read the same and confirming as social non-safe and outputting as such if the social safe signal of the portable device and the social safe signal of the nearby device are different.

In some embodiments of the invention system, optionally in combination with any or all the various embodiments disclosed herein, Module 100 is configured to allow inputting a social safe signal to a portable device by scanning a bar code, an image of document, or test strip or by manual inputting.

In some embodiments of the invention system, optionally in combination with any or all the various embodiments disclosed herein, the disease is COVID-19 infection or a sexually transmitted disease.

In some embodiments of the invention system, optionally in combination with any or all the various embodiments disclosed herein, the portable device is a smart phone or a note pad.

In some embodiments of the invention system, optionally in combination with any or all the various embodiments disclosed herein, the disease is HIV infection, HBv infection, or HBC infection.

In some embodiments of the invention system, optionally in combination with any or all the various embodiments disclosed herein, the social safe signal data is obtained by a COVID-19 virus RNA PCR test, by a blood IgG/IgM antibody test, by a saliva test, or by a stool test.

In some embodiments of the invention system, optionally in combination with any or all the various embodiments disclosed herein, the social safe signal data is obtained by a home testing kit.

DETAILED DESCRIPTION OF THE INVENTION

Definitions

Figure 1:
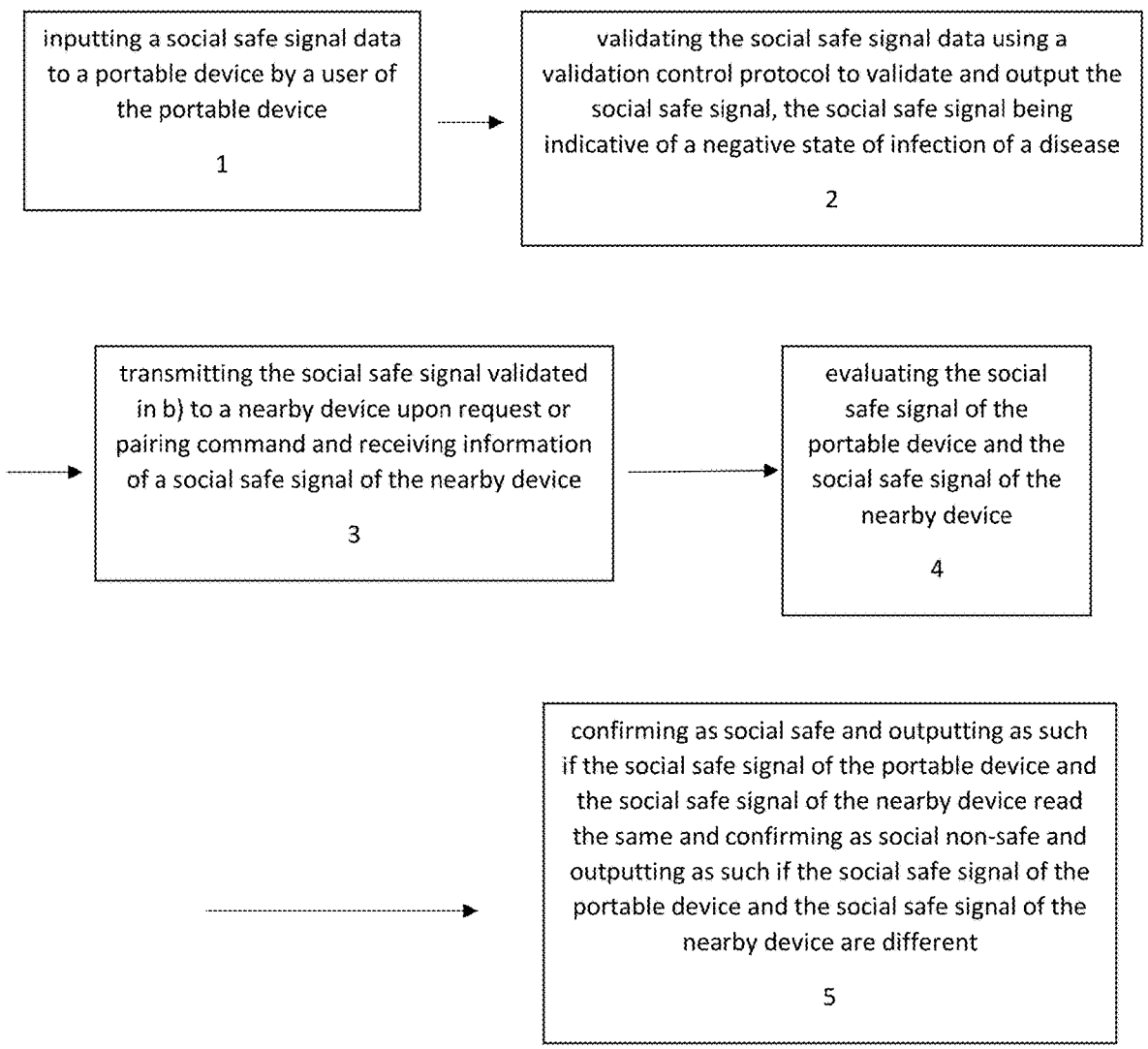
FIG. 1 illustrates an embodiment of the invention method.

As used herein, the term "social safe" refers to the health state of an individual that is safe to other people in social space, that is, the health state of the individual is one that would not bring infection risk exposure, or minimal level of infection risk exposure, to a nearby people in a social setting.

As used herein, the term "a user" shall mean user or owner of a portable device, which encompasses a family member of the user or owner of the portable device.

As used herein, the term "infection" or "infectious disease" shall be any disease caused by a microbial pathogen, e.g., bacteria, virus, or yeast, such disease being contagious in a social setting or contact of intimacy and capable of bringing about life threatening or serious condition to one being infected. Generally, such condition would require immediate or long-term medical attention such as COVID-19 infection or HIV infection, and sometimes, the attention of public health agencies.

As used herein, the term "digitally linking" or "digitally linked" shall mean any means of connection capable of transmitting or receiving digital information from one device to another. Examples of such include, e.g., linking (or linked) by a data cable, a phone line, cellular signals, wi-fi, GPS or satellite linking (e.g., SpaceX starlink), blue tooth connection or pairing of devices, and personal hotspot. In some embodiments, linking can be achieved by infrared transmission signals.

As used herein, the term "social safe signal data" shall mean test data obtained by testing the state of infection of a pathogen, e.g., COVID-19 or a sextually transmitted disease ("STD") such as HIV. Such testing data can be obtained from a laboratory testing or home testing.

As used herein, the term "home testing" refers to a home testing kit for an infectious condition, e.g., COVID-19 home testing kit based on swab samples taken from a cavity in the respiratory track, body fluid samples such as saliva, a blood sample, e.g., finger blood sample, or urine or stool samples.

As used herein, the term "validation control protocol" shall mean a set of rules or data or description capable of confirming social safe signal data of a user as one that indicates lacking infection of an infectious disease or having an degree of immunity against the infectious disease.

Social Safe Signal

In one aspect of the present invention, it is provided a method of social a method of social safe confirmation, comprising:

a) inputting a social safe signal data to a portable device by a user of the portable device, b) validating the social safe signal data using a validation control protocol to validate and output the social safe signal, the social safe signal being indicative of a negative state of infection of a disease, c) transmitting the social safe signal validated in b) to a nearby device upon request or pairing command and receiving information of a social safe signal of the nearby device, d) evaluating the social safe signal of the portable device and the social safe signal of the nearby device, and e) confirming as social safe and outputting as such if the social safe signal of the portable device and the social safe signal of the nearby device read the same and confirming as social non-safe and outputting as such if the social safe signal of the portable device and the social safe signal of the nearby device are different.

In some embodiments of the invention method, optionally in combination with any or all the various embodiments disclosed herein, inputting a social safe signal to a portable device is achieved by scanning a bar code, an image of document, or test strip or by manual inputting.

In some embodiments of the invention method, optionally in combination with any or all the various embodiments disclosed herein, the disease is COVID-19 infection or a sexually transmitted disease.

In some embodiments of the invention method, optionally in combination with any or all the various embodiments disclosed herein, the portable device is a smart phone or a note pad.

In some embodiments of the invention method, optionally in combination with any or all the various embodiments disclosed herein, the disease is HIV infection, HBv infection, or HBC infection.

In some embodiments of the invention method, optionally in combination with any or all the various embodiments disclosed herein, the social safe signal data is obtained by a COVID-19 virus RNA PCR test, by a blood IgG/IgM antibody test, by a saliva test, or by a stool test.

In some embodiments of the invention method, optionally in combination with any or all the various embodiments disclosed herein, the social safe signal data is obtained by a home testing kit.

FIG. 1 shows an embodiment of the invention method. Referring to FIG. 1, in step 1, a social safe signal data is inputted to a portable device by a user of the portable device. In step 2, validation of the social safe signal data is performed where the social safe signal data is validated using a validation control protocol to validate and output the social safe signal, the social safe signal being indicative of a negative state of infection of a disease. In step 3, the social safe signal validated in step 2 is transmitted to a nearby device upon request or pairing command and receiving information of a social safe signal of the nearby device. In step 4, the social safe signal of the portable device and the social safe signal of the nearby device are evaluated to see the states of infection or lack thereof match. In step 5, social safe is confirmed between the user of the portable device and the user of the nearby portable device and outputting as such if the social safe signal of the portable device and the social safe signal of the nearby portable device read the same and social safe is Not confirmed and outputting as social non-safe if the social safe signal of the portable device and the social safe signal of the nearby device are different.

Figure 4:
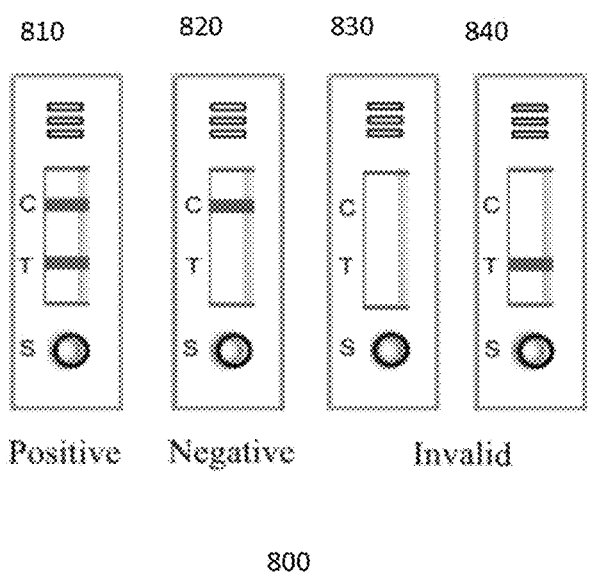
FIG. 4 shows an example of an embodiment of validation control protocol of invention.

FIG. 4 shows an embodiment of validation control protocol 800 in a blood testing kit. In FIG. 4, 810 shows a positive reading of a test strip of a blood sample where "S" indicates sample loading point, "C" denotes the position of an internal control line, and "T" denotes the position of the sample test line. When a blood sample was placed on the "S" point and pushed up the strip by a diluent (not shown), a line would show at the "C" position and another at the "T" position, indicating a positive reading. 820 shows a negative reading of a test strip of a blood sample where "S" again indicates sample loading point, "C" denotes the position of an internal control line, and "T" denotes the position of the sample test line. When a blood sample was placed on the "S" point and pushed up the strip by a diluent (not shown), a line would show at the "C" position and but no line shows at the "T" position, indicating a negative reading. Both 830 and 840 show invalid tests: in 830, no line shows on either "C" or "T" positions, and in 840, no line shows on the "C" position.

Software Program

In a second aspect of the present invention, it is provided a software program, comprising:

Module 100 configured to allow inputting a social safe signal data to a portable device by a user of the portable device, Module 200 configured to allow validating the social safe signal data using a validation control protocol to validate and output the social safe signal, the social safe signal being indicative of a negative state of infection of a disease, Module 300 configured to effect transmitting the social safe signal validated in b) to a nearby device upon request or pairing command and receiving information of a social safe signal of the nearby device, Module 400 configured to allow evaluating the social safe signal of the portable device and the social safe signal of the nearby device, and Module 500 configured to allow confirming as social safe and outputting as such if the social safe signal of the portable device and the social safe signal of the nearby device read the same and confirming as social non-safe and outputting as such if the social safe signal of the portable device and the social safe signal of the nearby device are different, wherein the software program is executable on the portable device.

In some embodiments of the invention software program, optionally in combination with any or all the various embodiments disclosed herein, Module 100 is configured to allow inputting a social safe signal to a portable device by scanning a bar code, an image of document, or test strip or by manual inputting.

In some embodiments of the invention software program, optionally in combination with any or all the various embodiments disclosed herein, the disease is COVID-19 infection or a sexually transmitted disease.

In some embodiments of the invention software program, optionally in combination with any or all the various embodiments disclosed herein, the portable device is a smart phone or a note pad.

In some embodiments of the invention software program, optionally in combination with any or all the various embodiments disclosed herein, the disease is HIV infection, a hepatitis infection such as HBv infection, or HBC infection.

In some embodiments of the invention software program, optionally in combination with any or all the various embodiments disclosed herein, the social safe signal data is obtained by a COVID-19 virus RNA PCR test, by a blood IgG/IgM antibody test, by a saliva test, or by a stool test.

In some embodiments of the invention software program, optionally in combination with any or all the various embodiments disclosed herein, the social safe signal data is obtained by a home testing kit.

Figure 2:
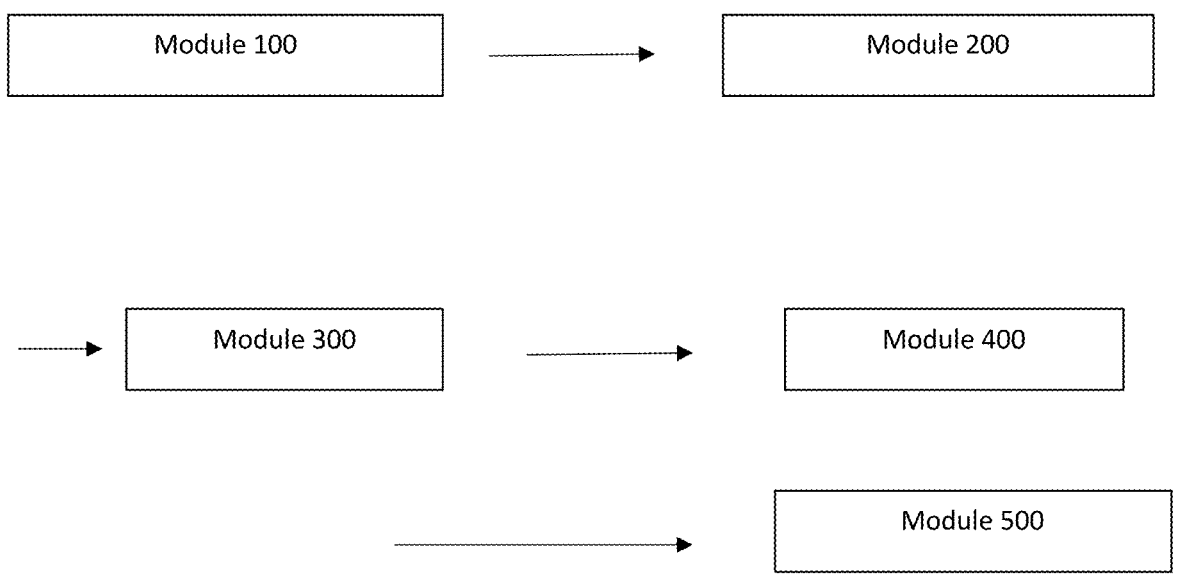
FIG. 2 illustrates an embodiment of the invention software program.

FIG. 2 shows an embodiment of the invention software program. Referring to FIG. 2, the software program includes Modules 100, 200, 300, 400 and 500. Module 100 is configured to allow inputting a social safe signal data to a portable device 700 by a user of the portable device 700, Module 200 configured to allow validating the social safe signal data using a validation control protocol 800 to validate and output the social safe signal, the social safe signal being indicative of a negative state of infection of a disease. Module 300 configured to effect transmitting the social safe signal validated in step 2 of the invention method as shown in FIG. 1 to a nearby device upon request or pairing command and receiving information of a social safe signal of the nearby device. Module 400 configured to allow evaluating the social safe signal of the portable device and the social safe signal of the nearby device. Module 500 configured to allow confirming as social safe and outputting as such if the social safe signal of the portable device and the social safe signal of the nearby device read the same and confirming as social non-safe and outputting as such if the social safe signal of the portable device and the social safe signal of the nearby device are different.

System

In a further aspect of the present invention, it is provided a system, comprising a plurality of portable devices digitally linked to a server,
wherein—
the server is configured to receive and process social safe signal data that a user of a portable device elects to transmit to the server; and
each of the portable devices comprises a software program executable on the portable device; and
wherein the software program comprises:
Module 100 configured to allow inputting a social safe signal data to a portable device by a user of the portable device,
Module 200 configured to allow validating the social safe signal data using a validation control protocol to validate and output the social safe signal, the social safe signal being indicative of a negative state of infection of a disease,
Module 300 configured to effect transmitting the social safe signal validated in b) to a nearby device upon request or pairing command and receiving information of a social safe signal of the nearby device,
Module 400 configured to allow evaluating the social safe signal of the portable device and the social safe signal of the nearby device, and
Module 500 configured to allow confirming as social safe and outputting as such if the social safe signal of the portable device and the social safe signal of the nearby device read the same and confirming as social non-safe and outputting as such if the social safe signal of the portable device and the social safe signal of the nearby device are different.

In some embodiments of the invention system, optionally in combination with any or all the various embodiments disclosed herein, Module 100 is configured to allow inputting a social safe signal to a portable device by scanning a bar code, an image of document, or test strip or by manual inputting.

In some embodiments of the invention system, optionally in combination with any or all the various embodiments disclosed herein, the disease is COVID-19 infection or a sexually transmitted disease.

In some embodiments of the invention system, optionally in combination with any or all the various embodiments disclosed herein, the portable device is a smart phone or a note pad.

In some embodiments of the invention system, optionally in combination with any or all the various embodiments disclosed herein, the disease is HIV infection, HBv infection, or HBC infection.

In some embodiments of the invention system, optionally in combination with any or all the various embodiments disclosed herein, the social safe signal data is obtained by a COVID-19 virus RNA PCR test, by a blood IgG/IgM antibody test, by a saliva test, or by a stool test.

In some embodiments of the invention system, optionally in combination with any or all the various embodiments disclosed herein, the social safe signal data is obtained by a home testing kit.

Figure 3:
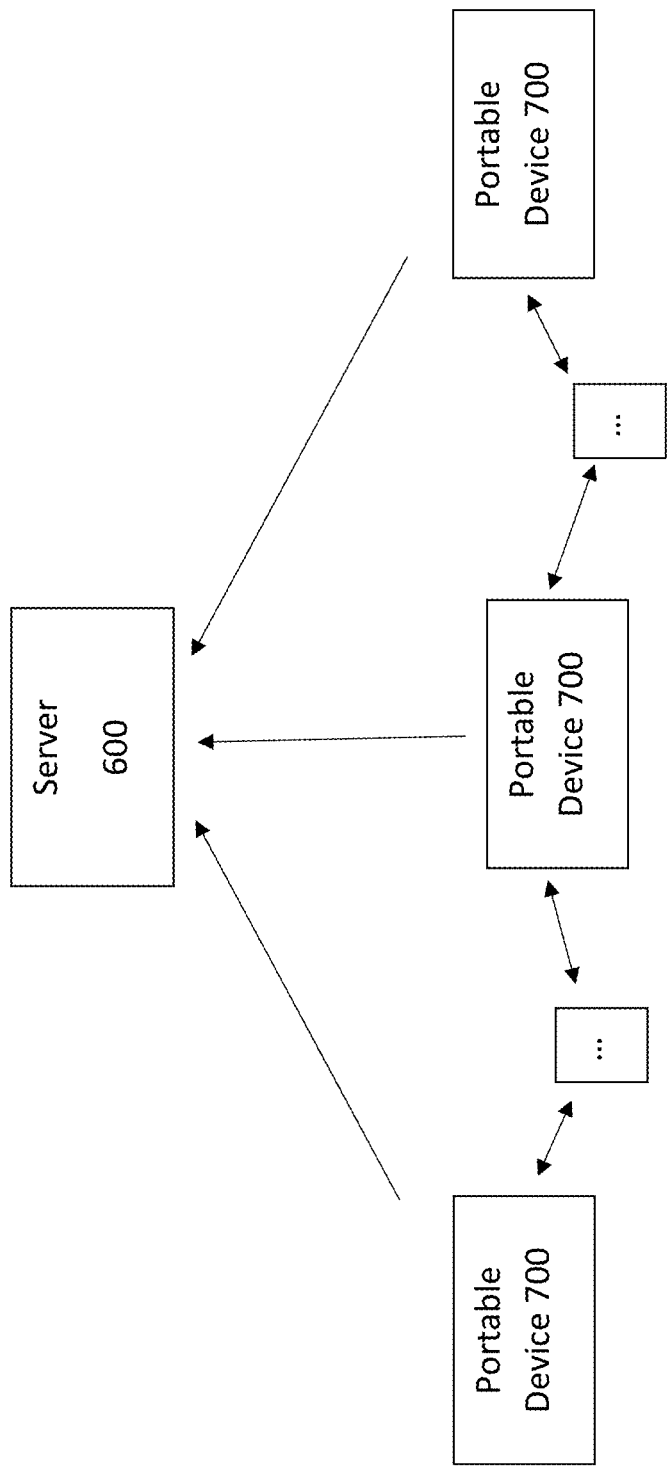
FIG. 3 illustrates an embodiment of the invention system.

FIG. 3 shows an embodiment of the invention system. Referring to FIG. 3, the system comprises a server 600, and a plurality of portable devices 700. The portable devices 700 are capable of communicating with each other, and each can communicate with the server 600. Server 600 can include a database (not shown) to accommodate the storage of user information of portable device 700 and processing of data information from a user of portable device 700. Database can be created anew or purchased from a commercial source, which is within the ordinary skill in the art.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

The following examples illustrate rather than limit the embodiments of the present invention.

Those skilled in the art will know, or be able to ascertain, using no more than routine experimentation, many equivalents to the specific embodiments of the invention described herein. These and all other equivalents are intended to be encompassed by the following claims.

I claim:
1. A method of social safe confirmation, comprising:
a) inputting a social safe signal data to a portable device by a user of the portable device,
b) validating the social safe signal data using a validation control protocol to validate and output a social safe signal, the social safe signal being indicative of a negative state of infection of a disease, c) transmitting the social safe signal validated in b) to a nearby device upon request or pairing command and receiving information of a social safe signal of the nearby device, d) evaluating the social safe signal of the portable device and the social safe signal of the nearby device, and e) confirming as social safe and outputting as such when the social safe signal of the portable device and the social safe signal of the nearby device read the same and confirming as social non-safe and outputting as such when the social safe signal of the portable device and the social safe signal of the nearby device are different.

2. The method according to claim 1, wherein inputting a social safe signal to a portable device is achieved by scanning a bar code, an image of document, or test strip or by manual inputting.

3. The method according to claim 1, wherein the disease is COVID-19 infection or a sexually transmitted disease.

4. The method according to claim 1, wherein the portable device is a smart phone or a note pad.

5. The method according to claim 1, wherein the disease is HIV infection, HBv infection, or HBC infection.

6. The method according to claim 1, wherein the social safe signal data is obtained by a COVID-19 virus RNA PCR test, by a blood IgG/IgM antibody test, by a saliva test, or by a stool test.

7. The method according to claim 1, wherein the social safe signal data is obtained by a home testing kit.

8. A system, comprising a plurality of portable devices digitally linked to a server, wherein— the server is configured to receive and process social safe signal data that a user of a portable device elects to transmit to the server; and each of the portable devices comprises a software program executable on the portable device; and wherein the software program is configured to allow or effect:

inputting a social safe signal data to a portable device by a user of the portable device, validating the social safe signal data using a validation control protocol to validate and output a social safe signal, the social safe signal being indicative of a negative state of infection of a disease, effect transmitting the social safe signal thus validated to a nearby device upon request or pairing command and receiving information of a social safe signal of the nearby device, evaluating the social safe signal of the portable device and the social safe signal of the nearby device, and confirming as social safe and outputting as such when the social safe signal of the portable device and the social safe signal of the nearby device read the same and confirming as social non-safe and outputting as such when the social safe signal of the portable device and the social safe signal of the nearby device are different.

9. The system according to claim 8, wherein the software program is configured to allow inputting a social safe signal to a portable device by scanning a bar code, an image of document, or test strip or by manual inputting.

10. The system according to claim 8, wherein the disease is COVID-19 infection or a sexually transmitted disease.

11. The system according to claim 8, wherein the portable device is a smart phone or a note pad.

12. The system according to claim 8, wherein the disease is HIV infection, HBv infection, or HBC infection.

13. The system according to claim 8, wherein the social safe signal data is obtained by a COVID-19 virus RNA PCR test, by a blood IgG/IgM antibody test, by a saliva test, or by a stool test.

* * * * *